United States Patent [19]

Mitchell et al.

[11] Patent Number: 5,408,315

[45] Date of Patent: Apr. 18, 1995

[54] GLOW DISCHARGE ANALYTICAL INSTRUMENT FOR PERFORMING EXCITATION AND ANALYZATION ON THE SAME SIDE OF A SAMPLE

[75] Inventors: Joel C. Mitchell, Bridgman, Mich.; Ted J. Casper, West Bend, Wis.

[73] Assignee: Leco Corporation, St. Joseph, Mich.

[21] Appl. No.: 99,144

[22] Filed: Jul. 28, 1993

[51] Int. Cl.$^6$ ............................................. G01J 3/443
[52] U.S. Cl. .................................. 356/311; 356/314; 356/316
[58] Field of Search ....................... 356/311, 316, 314; 250/288; 313/567, 622, 631, 632

[56] References Cited

U.S. PATENT DOCUMENTS

| | | | |
|---|---|---|---|
| 4,853,539 | 8/1989 | Hall et al. | 250/288 |
| 4,912,324 | 3/1990 | Clark et al. | 250/288 |
| 4,979,123 | 12/1990 | Yang | 356/311 |
| 5,006,706 | 4/1991 | Marcus | 250/288 |
| 5,028,133 | 7/1991 | Chevrier et al. | 356/311 |
| 5,086,226 | 2/1992 | Marcus | 250/288 |
| 5,172,183 | 12/1992 | Mega et al. | 356/311 |

OTHER PUBLICATIONS

"Diagnostics of an R.F. Sputtering Glow Discharge-...", International Journal of Mass Spectrometry and Ion Physics, 1975, pp. 129-138, by Eckstein et al.
"Luminescence of RF-Sputtered Oxide Films During Sputtering", by H. Ratinen, J. Appl. Phys., vol. 44, No. 9, Sep. 1973, pp. 3817-3820.
"Optical Spectroscopy for Diagnostics and Process...", by J. E. Greene, J. Vac. Sci. Technol., Sep./Oct. 1978, pp. 1718-1729.
"Glow Discharge Techniques in Analytical Chemistry," by W. W. Harrison et al., Analytical Chemistry, vol. 62, No. 18, Sep. 15, 1990, pp. 943-949.
"Glow Discharge Mass Spectrometry", by W. W. Harrison, University of Virginia, Chapter 3, Appendix B, pp. 85-123.
"Glow Discharge Processes, Sputtering and Plasma Etching", by Brian Chapman, Chapter 5, pp. 139-175.
"Radiofrequency Cavity Ion Source in Solids Mass Spectrometry", by D. L. Donohue et al., Analytical Chemistry, vol. 47, No. 9, Aug. 1975, pp. 1528-1531.
"Summary Abstract: Diagnostics in Plasma Processing," by J. W. Coburn, J. Vac. Sci. Technol., May/Jun. 1986, pp. 1830-1832.
"Glow Discharge Mass Spectrometry-Technique for Determining Elemental . . . ", by J. W. Coburn et al., Journal of Applied Physics, vol. 45, No. 4, Apr. 1974, pp. 177-184.
"The Formation of Complexes of the Type . . . ", by J. W. Coburn et al., The Journal of Chemical Physics, vol. 64, No. 2, Jan. 1976, pp. 907-908.
"Analytical Applications of Glow Discharge Devices," by K. R. Hess et al., Atomic Spectroscopy Advances, 5 pages.

Primary Examiner—F. L. Evans
Assistant Examiner—Jason D. Eisenberg
Attorney, Agent, or Firm—Price, Heneveld, Cooper, DeWitt & Litton

[57] ABSTRACT

A non-conductive isolator for supporting a sample to be analyzed by radio frequency energy induced glow discharge techniques has a conductive ring for coupling a source of radio frequency energy to the same surface of a sample which is in direct contact with the induced glow discharge. An adapter kit for converting a direct current glow discharge analysis apparatus to a radio frequency energy induced flow discharge is also disclosed as well as the method of analyzing non-conductive and sample conductive using a source of RF energy coupled to the same sample surface being analyzed.

24 Claims, 5 Drawing Sheets

GLOW DISCHARGE ANALYTICAL INSTRUMENT FOR PERFORMING EXCITATION AND ANALYZATION ON THE SAME SIDE OF A SAMPLE

BACKGROUND OF THE INVENTION

Commercial glow discharge atomic emission and mass spectrometer systems are generally limited to the analysis of conductive solid samples. In an attempt to develop glow discharge techniques for the analysis of non-conductive samples, research efforts have been made in the use of radio frequency powered sources for generating the glow discharge. U.S. Pat. Nos. 5,006,706 issued Apr. 9, 1991, and 5,086,226 issued Feb. 4, 1992, both invented by R. Kenneth Marcus at Clemson University under work sponsored by the National Science Foundation and U.S. Pat. No. 5,028,133 issued Jul. 2, 1991, to Michelle Chevrier et al. of France are representative of such work. All of the systems of these references rely on coupling the RF power through the sample, the sample is analyzed on one side and the RF power is applied to the opposite side. This method of analysis is limited in that the analytical signals will vary with elemental concentration (the desired relationship) and also with sample thickness (not a desired affect). This latter affect is due to the efficiency with which the RF power can be coupled to the analytical zone (portion of the sample that will be analyzed). This affect becomes important when attempting to compare analytical signals from different samples (which may not have the same thickness). As a result, the method is limited to samples of the same thickness or degraded analytical restfits are obtained from samples of differing thicknesses.

SUMMARY OF THE INVENTION

In accordance with the present invention, an RF powered glow discharge source is disclosed which applies the RF power to the same side of the sample upon which the analytical zone is located. Thus, the thickness of a sample no longer affects the analytical signal. Therefore, samples of any thickness may be analyzed freely.

These and other advantages, purposes and features of the invention will become more apparent from a study of the following description taken in conjunction with the drawing figures described below.

DETAILED DESCRIPTION OF THE PREFERRED EMBODIMENTS

Figure 1:
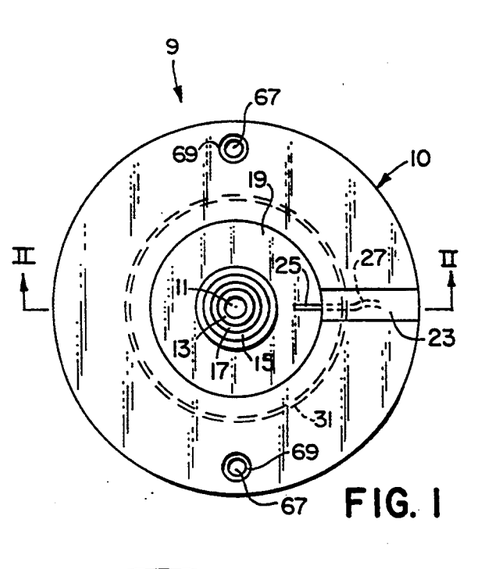
FIG. 1 is a plan view of the non-conductive isolator showing the electrical contact ring.
Figure 2:
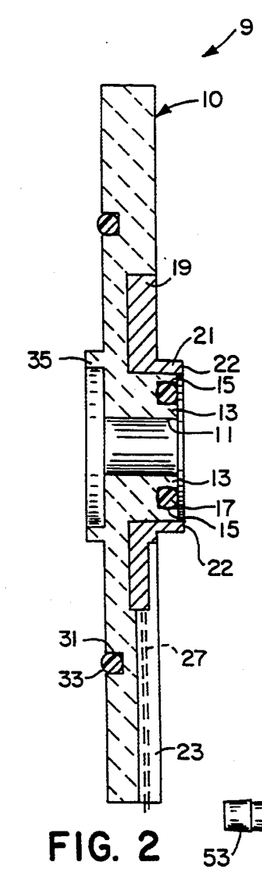
FIG. 2 is a sectional view of FIG. 1 taken along the plane II—II.

Referring to FIGS. 1 and 2, an interface assembly 9, including non-conductive isolator 10, is shown which can be attached to the cathode plate in a Grimm-type glow discharge lamp. Isolator 10 can be made of a suitable non-conductive material, such as ceramic, and is approximately 3 inches in diameter and ⅜ of an inch thick at the widest central portion. The isolator has a central aperture 11 which is bounded by a raised edge 13. A groove 15 is provided adjacent edge 13 into which an elastic sealing member such as an O-ring 17 is positioned. A preferably circular, electrical contact member 19 surrounds the raised portion of the isolator and is recessed into the insulating material forming the isolator. Electrical contact member 19 has a raised annular ring portion 21. The top face 22 of the annular ring projects outwardly approximately 0.005 inch beyond the top face of edge 13 to provide a uniform electrical contact with the face of the sample. While a circular electrical contact member is preferred, the contact can be other configurations such as an aperture in a rectangular contact pad or multiple contact pads spaced about the aperture in the isolator. The important criteria is that the contact provides a substantially uniform contact with the glow discharge region.

A radial, recessed channel 23 is provided in the surface of the isolator for an electrical contact to be inserted to make contact with conductive ring 19 at slot 25. A copper wire 27 (FIG. 2) can be inserted into groove 23 with the end of the wire either silver soldered to contact 19, or connected by a suitable threaded member, such as a screw (not shown).

On the opposite face of isolator 10 is a circular groove 31 (FIG. 2) in which an O-ring 33 is positioned for forming a gas-tight seal with the face of the cathode. Near the central portion of the isolator is a raised circular ridge 35 which fits into a circular groove 37 (FIG. 3) for aligning aperture 11 of isolator 10 with the aperture 38 in cathode 40.

Figure 3:
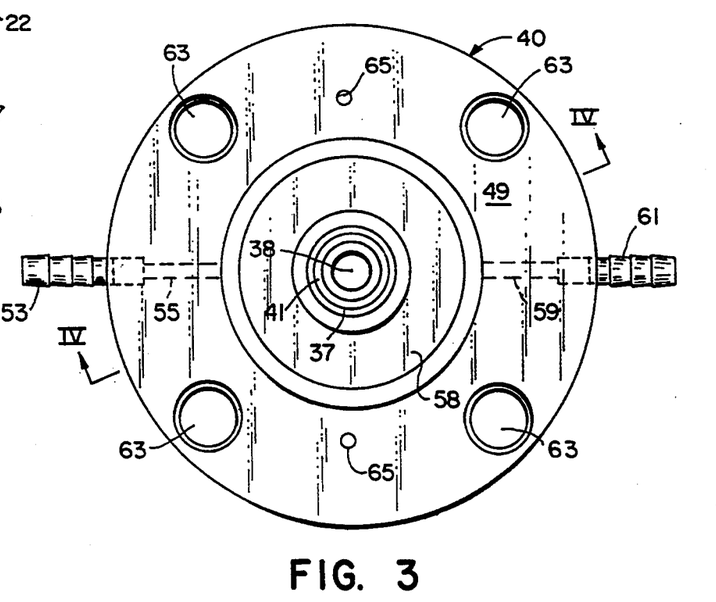
FIG. 3 is a plan view of a cathode with internal water cooling.
Figure 4:
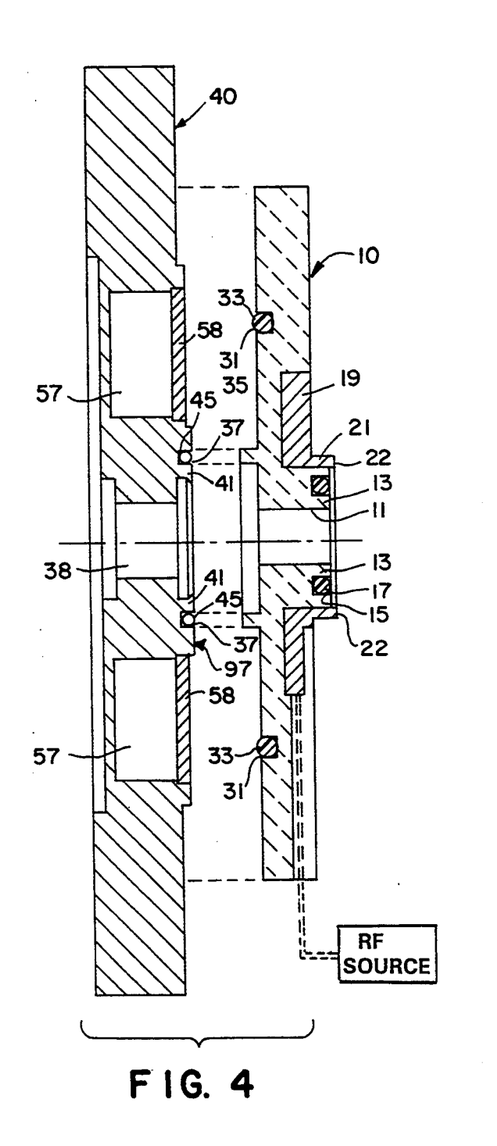
FIG. 4 is an exploded sectional view showing isolator spaced form a cathode taken along plane IV—IV in FIG. 3.

As shown in FIG. 3, cathode 40 is of a circular configuration approximately 4¼ inches in diameter. The cathode is also approximately ½ inch thick. The cathode, as shown in FIG. 3, is suitable for use in the analysis of conductive samples where the sample would be placed over aperture 38 and held tightly in place by atmospheric pressure forcing the sample against the surface of the aperture in view of the reduced pressure inside the glow discharge apparatus. Bounding aperture 38 is raised annular ring 41 (best shown in FIG. 4) which has a planar sample contacting surface. Groove 37 surrounds ring 41. An O-ring or other elastic seal 45 can be placed in groove 37.

In view of the heat generated in the cathode during the glow discharge process, a cooling water inlet 53 (FIG. 3) is provided through which water can enter into an internal conduit 55 leading to a cooling chamber 57 (FIG. 4) which surrounds the area occupied by the sample during the glow discharge process. Cooling chamber 57 is sealed by a disc 58. Water can exit chamber 57 through an internal conduit 59 and an external nipple 61. A plurality of spaced apertures 63 are provided in the cathode for insulated bolts to pass for attachment of the cathode to the anode of the glow discharge apparatus. Threaded apertures 65 are provided for the attachment of non-conductive isolator 10. Isolator 10 has a pair of apertures 67 (FIG. 1) which are bounded by sloping surface portions 69. A flat-headed screw, having sloping shoulders, can be conveniently screwed into apertures 65 in cathode 40 to attach the isolator to the cathode with the screws flush against the surface of isolator 10.

Raised ridge 35 (FIG. 7) on the other face of isolator 10 is designed to tit into and interlock with circular groove 37 in the face of a cathode. By so fitting the cathode and isolator together, apertures 11 and 38 are aligned. Groove 37 would normally hold O-ring 45 when cathode 40 was being used as a DC Grimm-type glow discharge lamp with a conductive sample pressed against ring 41. O-ring 45 would provide a resilient seal between the sample and the cathode.

Figure 5:
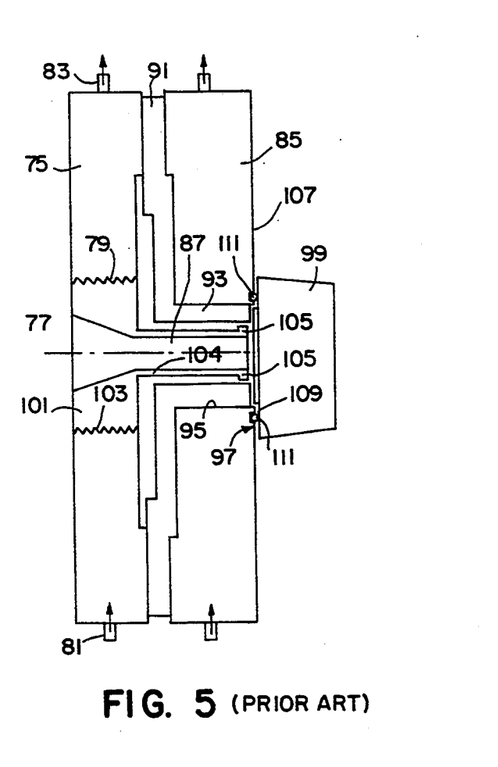
FIG. 5 is a schematic sectional view of a prior art DC glow discharge source with cross-hatching omitted for clarity.

Referring now to FIG. 5, a prior art direct current (DC) glow discharge source will be described having an anode 75 with an aperture 77 therein. Aperture 77 is bounded by a threaded wall 79. In order to cool the anode during operation of the glow discharge source, cooling water can enter through a port 81 and exit through a port 83. The glow discharge source has a cathode 85 which has an aperture 87 therein. An insulating member 91, having a tubular projecting portion 93, covers most of the wall 95 which bounds aperture 87 in cathode 85. A small annular portion of the cathode surface 97 is exposed adjacent to conductive sample 99.

An anode insert member 101 has a threaded outer surface 103 which enables the insert member to be threaded into anode 75. Anode insert 101 has a projecting tubular portion 104 which passes through aperture 87 in the center of the cathode and insulating member 91. Anode insert member 101 has an annular, flat surfaced, projecting ring portion 105 which is positioned close to conductive sample 99. The outer face 107 of cathode 85 has a circumferential groove 109 bounding the aperture in the cathode. An O-ring 111 or other elastic seal member can be placed in groove 109 to provide a gas-tight seal between sample 99 and the glow discharge source.

In operating the DC glow discharge source of FIG. 5, a DC potential is applied between anode 75 and cathode 85. Insulating member 91 shields a major portion of face 95 of aperture 87 in cathode 85. A glow discharge can form between the anode insert 101 and exposed portion of sample 99. The glow discharge will generate ions of inert gas which will bombard the face of sample 99 causing a glow to form as electrons in excited atoms of the sample drop back to a lower energy state causing a glow to be emitted characteristic of the composition of the elements in sample 99. Sample 99 is in contact with cathode 85 and, as previously mentioned, is conductive and, in effect, forms a portion of the cathode of the glow discharge device.

Figure 6:
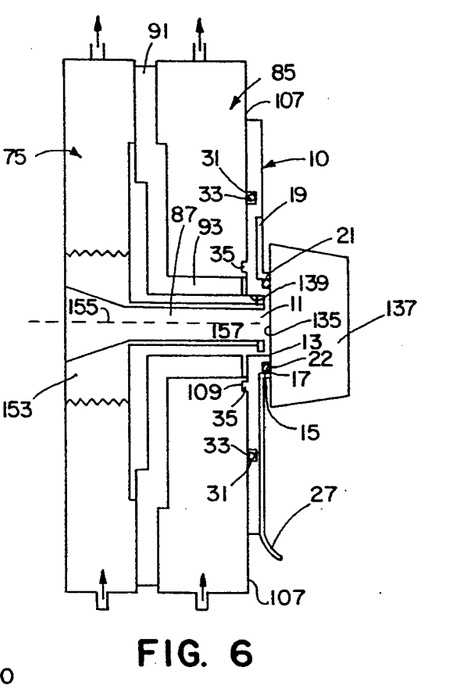
FIG. 6 is a schematic sectional view of the RF glow discharge source of the present invention with cross-hatching omitted for clarity.

In order to analyze a non-conductive sample by glow discharge techniques, the preferred method is to use RF current to generate the glow discharge. Referring to FIG. 6, an RF glow discharge apparatus is shown which uses several of the components from the DC glow discharge device shown in FIG. 5 and, therefore, identical reference numerals will be used for the common elements. In general there is an anode 75 and a cathode 85 which are separated by an insulating member 91 which has a tubular portion 93 substantially covering the wall bounding aperture 87 in cathode 85.

An insulating isolator 10 is attached to surface 107 of cathode 85 by suitable threaded fasteners (not shown). Isolator 10, as described above, is made from a suitable insulating material, such as a ceramic material, to provide electrical insulation and withstand the heat generated during the glow discharge process. On the side of isolator 10, facing surface 107 of cathode 85, is a circumferential projecting portion 35 which locks into groove 109 which formerly contained O-ring 111 (FIG. 5). By locking the isolator into this same groove, aperture 11 in the insert member is precisely aligned with the apertures through anode 75 and cathode 85. A circumferential groove 31 is provided on the face of isolator 10 for receiving an O-ring 33 to provide a gas-tight seal between the isolator and the interior of the glow discharge apparatus.

On the opposite surface of isolator 10 is, preferably, a planar metallic ring 19 having a raised annular edge 21 for providing contact with the surface 135 of sample 137. Aperture 11 in isolator 10 is bounded by a non-conductive face 139 which terminates in a circumferential projecting edge 13. Edge 13 defines a groove 15 in which an O-ring 17 can be positioned to provide a gas-tight seal between surface 135 of sample 137 and the interior of the glow discharge apparatus. Annular metal contact surface 22 is approximately 0.005 inch higher than non-conductive edge 13. The raised metal ring provides a uniform contact with the face of the sample to be subjected to the glow discharge analysis. As previously mentioned in regard to FIG. 1, the surface of the isolator has a recessed channel in which an electrical conductor 27 can be inserted and attached to the edge of metal contact (not shown).

Anode 75 has a threaded insert 153 which has an elongated central tubular portion which extends through aperture 87 in cathode 85 and substantially through aperture 11 in isolator 10 to position the end of the anode insert close to sample 137. A conductive annular collar 157 surrounds the end of the tubular portion of anode insert 153.

The gap from anode insert collar 157 to face 135 of the cathodically connected sample should be approximately 0.12 min. The concentric gap about collar 157 and insulating wall 139 should be the same distance. The concentric gap should be carefully machined. The end of the anode insert is made slightly larger and is then brought back to size by a facing tool working off the circumferential face in the insert member for positioning. By maintaining this close spacing the probability of plasma forming in the gap goes to zero. This area is also frequently referred to as a "dark space."

It is important to note that isolator edge 13 substantially shields electrical contact surface 19 from active ions during the glow discharge process. Raised ridge 13 effectively prevents the metal components of contact 19 from appearing in the glow discharge spectra of the sample being analyzed.

Figure 7:
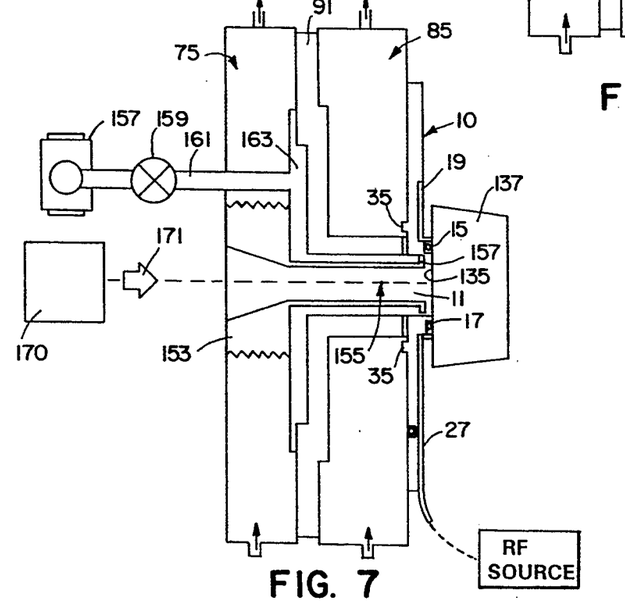
FIG. 7 is a schematic view of the apparatus of FIG. 6 with a vacuum source and spectrometer shown in block diagram form with cross-hatching omitted for clarity.

In the operation of the device, and referring to FIG. 7, anode 75, cathode 85, isolator 10 and anode insert 153 are assembled together as shown in FIG. 6. Non-conductive sample 137, after having been given suitable surface polishing using several sizes of grit, is pressed against O-ring 17 and then the interior of the glow discharge apparatus is evacuated. The atmospheric pressure pushing against sample 137 will hold it in place against the electrical contact surface 22 on isolator 10. The anode and cathode are at zero DC potential. A source of RF energy of approximately 100 watts at 13.56 MHz can be applied to conductor 27, electrical contact 19 and the face 135 of sample 137. The glow discharge will then form between the anode insert and the sample. During the glow discharge process, material is sputtered from the Face of the sample. In order to remove this material a vacuum pump 157 (FIG. 7) is connected through a valve 159 to a conduit 161 which leads to the interior 163 of the glow discharge cell and the sample face. By pumping out approximately 50 ml per minute of Argon gas, the sputtered material will be drawn away from the sample face enabling a fresh sample surface to be continually presented for analysis.

As mentioned above, the glow discharge is generated in area 155 of the anode insert tube. The analysis is carried out with a suitable spectrometer 170 which is focused, as shown by arrow 171, to look down through the bore of the aperture in the apparatus directly at the glow discharge region. It could be said that the spectrometer is bore sighted onto the glow discharge with the anode insert tube providing the bore.

Referring now to FIGS. 8–11, an alternate embodiment of the interface assembly 209 is shown which can be attached to the cathode plate in a Grimm-type glow discharge lamp. Interface assembly 209 includes an isolator 210 made of a suitable non-conductive material, such as MACOR, a ceramic, and is approximately 1.75 inches in diameter and ¼ of an inch thick at the widest central portion. The isolator has a central aperture 211 which is bounded by a raised edge 213. A groove 215 is provided adjacent edge 213 into which a circular, electrical contact member 219 is loosely positioned. Contact 219 has an external diameter approximately 0.01 inch smaller than the outer diameter of groove 215 to allow for expansion of the contact during use. The dimensions and shape of contact 219 may be changed to vary the air gap in groove 215 between contact 219 and isolator 210 to vary the capacitive coupling between contact 219 and cathode 240. Contact 219 is manufactured from any suitable material such as copper.

Figure 8:
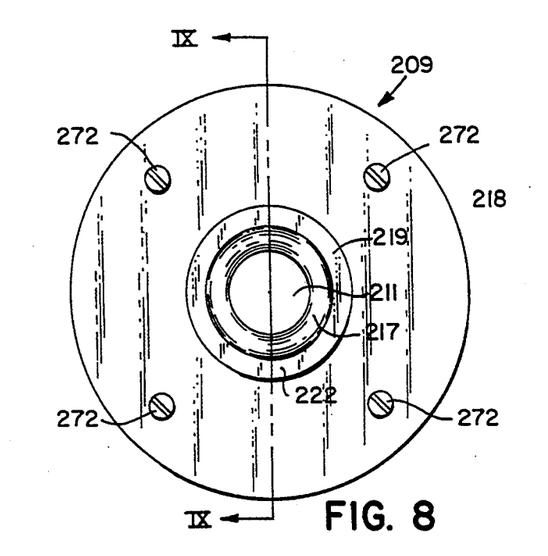
FIG. 8 is a plan view an alternative embodiment of a non-conductive interface.
Figure 9:
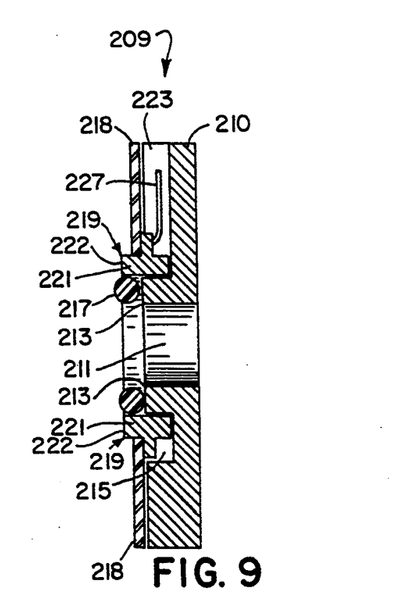
FIG. 9 is sectional view of FIG. 8 taken along plane IX—IX in FIG. 8.
Figure 10:
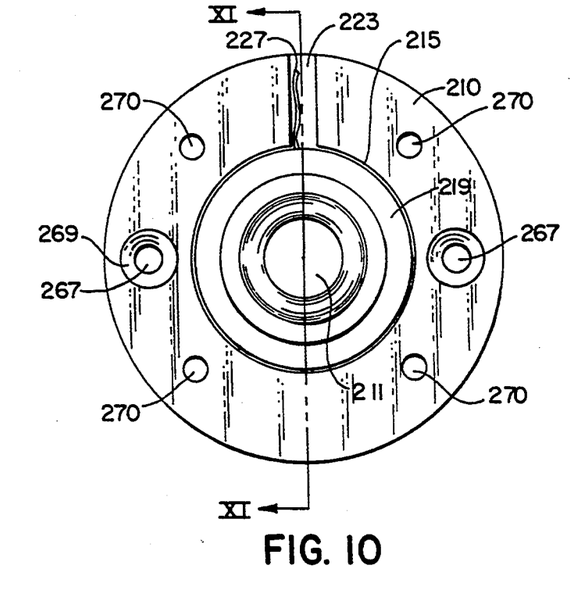
FIG. 10 is a plan view of the insulator according to FIG. 8 with a retainer removed.
Figure 11:
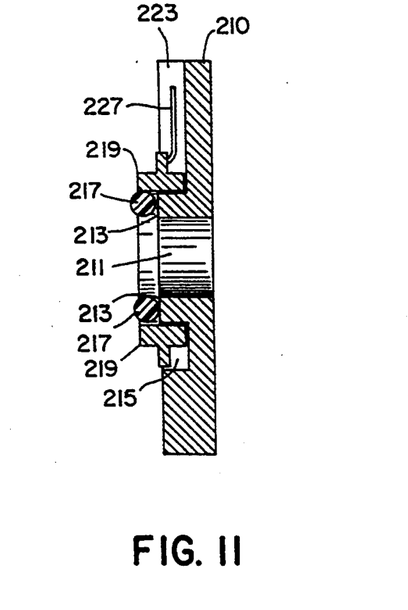
FIG. 11 is a sectional view of FIG. 10 taken along plane XI—XI in FIG. 10.
Figure 13:
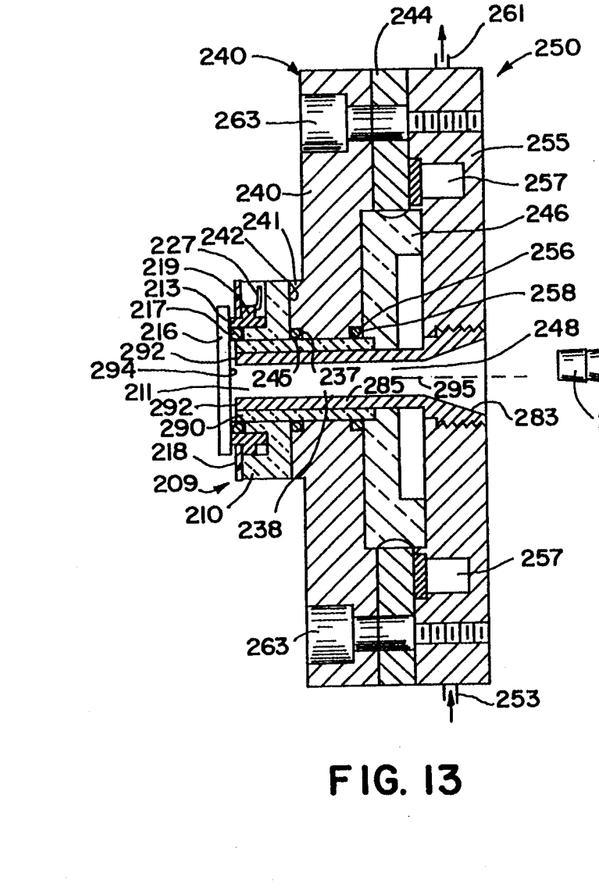
FIG. 13 is a sectional view of the interface according to FIG. 12 taken along plane XIII—XIII in FIG. 12.

Contact 219 surrounds the edge 213 of isolator 210 and projects outwardly therefrom. Contact 219 is also received into the insulating material forming the isolator. Electrical contact 219 has a raised annular ring portion 221 which forms one of four sides for an elastic seal such as an O-ring 217. The top face 222 of the contact 219 projects outwardly approximately 0.065 inch beyond the top face of edge 213 to provide a uniform electrical contact with the face of a sample 216 (FIG. 13). While a circular electrical contact member is preferred, the contact can be other configurations such as an aperture in a rectangular contact pad or multiple contact pads spaced about the aperture in the isolator. The important criteria is that the contact provides a substantially uniform contact concentric to the glow discharge region. Contact 219 is held in isolator 210 by a retainer 218 (FIG. 8). Retainer 218 is preferably secured to isolator 210 using NYLON fasteners 272 such as NYLON threaded fasteners. The retainer may be constructed of any suitable non-conductive material such as TEFLON or NYLON.

A recessed channel 223 is provided in the surface of the isolator 10 for an electrical contact (not shown) to be inserted such that it makes contact with conductive ring 219. A copper wire 227 can be inserted into groove 223 with the end of the wire either silver soldered to contact 219, or connected by a suitable threaded member, such as a screw (not shown). The opposite face of isolator 210 is substantially planar to contact an O-ring 245 (FIG. 13) to form a gas-tight seal with the face of the cathode 240.

Figure 12:
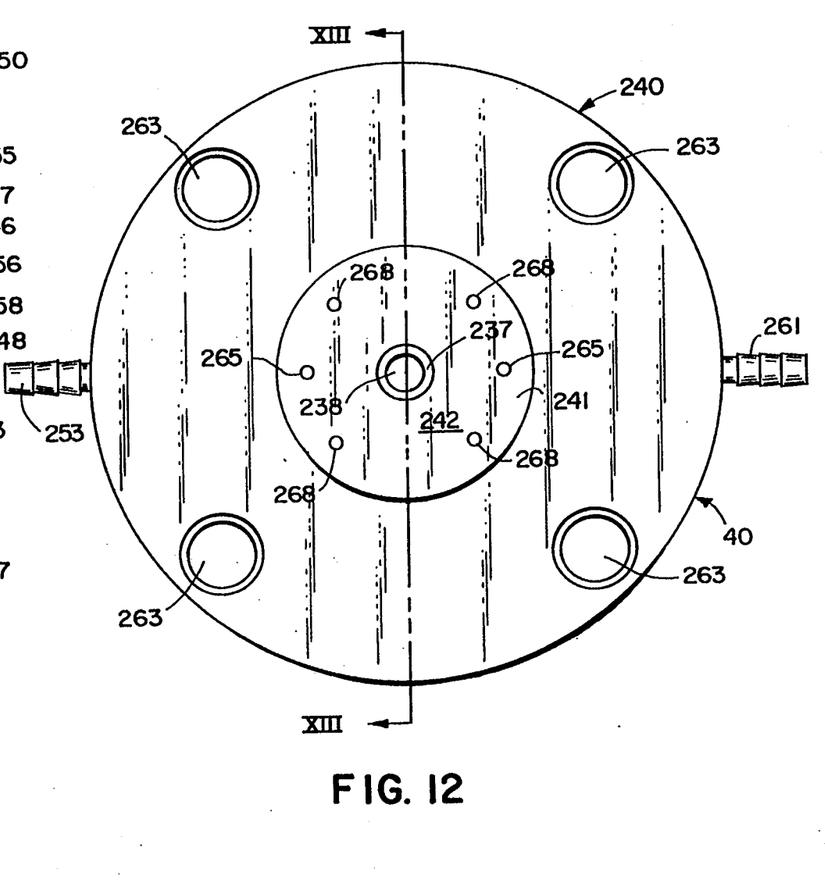
FIG. 12 is a top plan view of a glow-discharge lamp including the interface according to FIG. 8.

As shown in FIG. 12, cathode 240 is of a circular configuration approximately 4⅛ inches in diameter. The cathode is approximately ½ inch thick. The cathode, as shown in FIG. 12, is suitable for use in the analysis of non-conductive samples and mates with a conventional anode 255. A central aperture 238 is provided in the cathode. A raised annular ring 241 has a planar contacting surface 242 for contacting isolator 210. Groove 237 circumscribes the interior of ring 241. An O-ring or other elastic seal 245 is placed in groove 237 to seal the joinder of cathode 240 and isolator 210. The opposite face of cathode 240 includes a circumferential groove 256 for receipt of a resilient gas sealing member, such as O-ring 258.

The glow discharge lamp 250 for use with assembly 209 includes an electrically conductive spacer disc 244 positioned therebetween. The electrically conductive disc can be manufactured from any suitable material, and may be manufactured from the same material as anode 255 or cathode 240. Even though the cathode 240 and anode 255 are electrically connected by member 242, and are preferably connected to zero volts, the "anode" and "cathode" label are retained in the description of this embodiment since these discs are physically positioned in the location of the anode and cathode of traditional Grimm-type lamps. Disc 244 includes a round, central opening which receives a precision spacer 246. The precision spacer is a circular member manufactured of a suitable material, and may for example be manufactured of a macor ceramic. The spacer includes a central aperture 248 for alignment with openings 238.

In view of the heat generated during the glow discharge process, a cooling water inlet 253 (FIG. 12) is provided in anode 255 through which water can enter into an internal conduit (not shown) leading to a cooling chamber 257 (FIG. 13). Water can exit this area through an internal conduit (not shown) and an external nipple 261. A plurality of spaced apertures 263 are provided in the inner electrode for insulated bolts to pass for attachment of the cathode 240 to the anode 255 of the glow discharge lamp. Threaded apertures 265 (FIG. 12) are provided for the attachment of non-conductive isolator 210. Isolator 210 has a pair of apertures 267 (FIG. 10) which are bounded by sloping surface portions 269. A flat-headed screw (not shown), having sloping shoulders, can be conveniently screwed into apertures 265 in inner electrode 240 to attach the isolator to the cathode with the screws flush against the surface of isolator 210. Cathode 240 includes threaded apertures 268 for attachment of retainer 218. Isolator 210 also includes apertures 270 (FIG. 10) for passage of a threaded fastener 272 (FIG. 8) securing retainer 218 on the assembly.

As mentioned above, in order to analyze a non-conductive sample by glow discharge techniques, the preferred method is to use RF current to generate the glow discharge. An insulating isolator 210 is attached to surface 242 of cathode 240 by suitable threaded fasteners (not shown). Isolator 210 is made from a suitable insulating material, such as a ceramic material, to provide electrical insulation and withstand the heat generated during the glow discharge process. The surface of isolator 210, facing surface 242 of cathode 240, is flat and abuts O-ring 245 to form a seal. The isolator 210 is positioned by the threaded fasteners (not shown) inserted into aperture 267 and threaded aperture 265 (FIG. 12).

With reference now to FIG. 13, anode 255 has a threaded insert 283 which has an elongated central tubular portion 285 which extends through aperture 248 in cathode 240 and substantially through aperture 211 in isolator 210 to position the end of the anode insert close to sample 216. A cylindrical insulator tube 290, made of a suitable non-conductive material, such a ceramic, is positioned between the anode insert and members 240 and 210 and a portion of member 246. The cylinder provides an insulating wall.

The gap from anode insert tip 292 to face 294 of the connected sample 216 should be approximately 0.12 mm. By maintaining this close spacing the probability of plasma forming in the gap goes to zero. This area is also frequently referred to as a "dark space."

It is important to note that isolator edge 213 and tube 290 substantially shield electrical contact surface 219 from active ions during the glow discharge process. They effectively prevent the metal components of contact 219 from appearing in the glow discharge spectra of the sample being analyzed.

In the operation of the device, and referring to FIG. 13, anode 255, cathode 240, isolator 210 and anode insert 283 are assembled together as shown in FIG. 13. Non-conductive conductive sample 216 is pressed against O-ring 217 and then the interior of the glow discharge apparatus is evacuated. The atmospheric pressure pushing against sample 216 will hold it in place against the electrical contact surface 222 on interface assembly 209. The anode and cathode are at zero DC potential. A source of RF energy of up to approximately 100 watts at 13.56 MHz can be applied to conductor 227, electrical contact 219 and the inner surface of sample 216. The glow discharge will then form between the anode and the sample in region 295 within the anode insert. During the glow discharge process, material is sputtered from the face of the sample. In order to remove this material a vacuum pump such as that shown in FIG. 7 may be utilized.

It can clearly be seen that by use of the apparatus of the present invention the sample face being analyzed is the same face in contact with the source of RF energy. By viewing the same face, thickness effects of the sample which previously complicated the process and tended to lead to inaccurate data, is eliminated. The analytical instrument looks directly at the glow discharge caused by active atoms from the face of the sample being analyzed.

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modification.

The embodiments of the invention in which an exclusive property or privilege is claimed are defined as follows:

1. An apparatus for use in the analysis of non-conductive and conductive samples by glow discharge technique comprising:
   a chamber for containing an ionizable gas;
   an anode disposed in said chamber, said anode having an aperture therein;
   a cathode spaced from said anode, said cathode having an aperture therein in alignment with said aperture in said anode and forming with said aperture in said anode an axial passage;
   an isolator abutting said cathode for holding a sample to be analyzed in line with said axial passage through said anode and cathode;
   an electrical contact member on said isolator for contacting a side of a sample facing said axial passage; and
   an RF energy source operably coupled to said electrical contact member for providing ratio frequency energy to a sample in contact therewith and producing an ionized gas which travels through said axial passage to contact a surface of said sample in contact with said electrical contact member.

2. An apparatus as set forth in claim 1, wherein said electrical contact member is substantially shielded by said isolator from gas ions in said axial passage.

3. An apparatus as set forth in claim 1, wherein said electrical contact member comprises an electrically conductive ring disposed on a surface of said isolator.

4. An apparatus as set forth in claim 3, wherein said electrically conductive ring includes a raised annular sample contacting portion bounding an aperture in said electrically conductive ring.

5. An apparatus as set forth in claim 4, wherein said electrically conductive ring is disposed on a surface of said isolator with said raised annular sample contacting portion of said electrically conductive ring projecting outwardly from said surface of said isolator.

6. An apparatus as set forth in claim 3, wherein said isolator includes an aperture therein aligned with said axial passage in said anode and cathode and an annular groove spaced from and surrounding said aperture for receiving and supporting an elastic sealing member for forming a gas-tight seal with a surface of said cathode.

7. An apparatus set forth in claim 6, wherein said cathode includes a first surface spaced from said anode and a second surface on the opposite side of said cathode with an annular groove therein surrounding said aperture in said cathode and, said isolator including a raised circular portion interlocking with said annular groove in said second cathode surface and aligning said aperture in said isolator with said aperture in said cathode.

8. An apparatus as set forth in claim 5, wherein said isolator includes a raised annular edge bounding said aperture in said isolator which edge is spaced from and surrounding said raised annular sample contacting portion of said electrically conductive ring for forming a groove for receiving and supporting an elastic sealing member used to form a gas-tight seal with said surface of said sample.

9. An apparatus as set forth in claim 8, wherein said raised annular edge of said isolator shields a side of said raised annular sample contacting portion of said electrically conductive ring from contact by gas ions.

10. An isolator for supporting a non-conductive sample for analysis by an apparatus using radio frequency induced glow discharge techniques comprising:
  a isolator having an aperture therein and a first surface configured to cooperate with a surface of a cathode member, having an aperture therein, for locating said aperture in said isolator in alignment with said aperture in said cathode member;
  an electrically conductive member disposed on a second surface of said isolator adjacent said aperture in said isolator, said electrically conductive member providing an electrical connection to one face of a sample which is to be subjected to said glow discharge analysis technique; and
  a raised portion on said second surface of said isolator adjacent said aperture in said isolator, and configured to substantially shield said electrically conductive member from contact with said glow discharge.

11. An isolator as set forth in claim 10, wherein said electrically conductive member comprises a ring having a raised sample contacting portion bounding an aperture in said ring.

12. An adapter kit for converting a direct current glow discharge analysis apparatus to a radio frequency induced glow discharge analysis apparatus comprising:
  an isolator for attachment to a face of a cathode of said apparatus, said isolator having an aperture therein aligned with an aperture in said cathode;
  a conductive coupling ring on a surface of said isolator for electrically connecting a source of radio frequency energy to a surface of a sample which is in direct contact with the induced glow discharge; and
  a tubular anode insert member for attachment to an anode of said apparatus for extending through said aperture in said isolator to a location closely adjacent to the surface of the sample.

13. A radio frequency current glow discharge source for the analysis of a sample using glow discharge techniques comprising:
  an anode member having an aperture therein;
  a cathode member adjacent to said anode member, said cathode member including an aperture therein and a circular groove in a face remote from said anode member, said groove surrounding said aperture in said cathode member;
  an insulating member disposed between, and electrically separating said anode member and said cathode member, said insulating member including a projecting tubular portion defining a aperture, said projecting tubular portion extending through said aperture in said cathode member and covering all but an annular portion of said aperture in said cathode member;
  an isolator for attachment to said cathode member, said isolator having an aperture therein aligned with said aperture in said insulating member;
  an electrical contact member on a surface of said isolator remote from said cathode member for electrically connecting a source of radio frequency energy to a sample which is in direct contact with said glow discharge; and
  a tubular anode insert member or attachment to said anode member and extending through said aperture in said insulating member and through said aperture in said isolator to a location proximate to said sample.

14. A ratio frequency current glow discharge as set forth in claim 13, wherein said aperture in said anode member is threaded and said anode insert member is threaded for threaded attachment to said anode member.

15. A radio frequency current glow discharge source as defined in claim 13, wherein said electrical contact member is substantially shielded by said isolator from gas ions.

16. A radio frequency current glow discharge source as defined in claim 13, wherein said electrical contact member comprises an electrically conductive ring disposed on a surface of said isolator.

17. A radio frequency current glow discharge source as defined in claim 16, wherein said electrical contact member comprises a raised annular sample contacting portion bounding an aperture in said electrically conductive ring.

18. A radio frequency current glow discharge source as defined in claim 17, wherein said electrically conductive ring is disposed on the surface of said isolator with said raised annular sample contacting portion of said ring projecting outwardly from said surface of said isolator.

19. A radio frequency current glow discharge source as defined in claim 18, wherein said isolator includes an annular groove spaced from and surrounding said aperture therein for receiving and supporting an elastic sealing member for forming a gas-tight seal with a surface of said cathode member.

20. A radio frequency current glow discharge source as defined in claim 19, wherein said raised annular edge of said isolator shields a side of said raised annular sample contacting portion of said electrically conductive ring from contact by gas ions.

21. A radio frequency current glow discharge source as defined in claim 18, wherein said isolator has a raised annular edge bounding said aperture in said isolator which edge is spaced from said raised annular sample contacting portion of said electrically conductive ring for forming a groove for receiving and supporting an elastic sealing member used to form a gas-tight seal with a surface of a sample.

22. A radio frequency current glow discharge source as defined in claim 13, wherein said cathode member includes a first surface spaced from said anode member and a second surface on the opposite side of said cathode member having an annular groove therein surrounding said aperture in said cathode member and, said isolator including a raised circular portion for interlocking with said annular groove in said second cathode surface for aligning said aperture in said isolator with said aperture in said cathode member.

23. A method for the analysis of a sample by radio frequency current induced glow discharge, comprising the steps:
  providing a glow discharge apparatus having an anode and a cathode with aligned apertures therein;
  attaching an isolator with an aperture therein to said cathode with the aperture in said isolator aligned with the aperture through said anode and cathode;
  providing an electrical contact member on the side of said isolator remote from said cathode;
  affixing a surface of the sample to be analyzed to said electrical contact member so as to close said aperture in said isolator;

generating a glow discharge adjacent to said surface of the sample in electrical contact with said electrical contact member; and analyzing said glow discharge by viewing through said apertures in said anode, cathode, and isolator.

24. The method of claim 23, including the additional step of applying a vacuum source to the vicinity of said glow discharge to remove sputtered sample material to provide a clean sample surface for analysis.

* * * * *

UNITED STATES PATENT AND TRADEMARK OFFICE
CERTIFICATE OF CORRECTION

PATENT NO. : 5,408,315
DATED : April 18, 1995
INVENTOR(S) : Joel C. Mitchell, et al It is certified that error appears in the above-indentified patent and that said Letters Patent is hereby corrected as shown below:

Column 1, line 35;

"restfits" should be --results--.

Column 2, line 65;

After "is" insert --a--.

Column 3, line 21;

"tit" should be --fit--.

Column 4, line 54;

"min." should be --mm.--.

Column 7, line 19;
(2nd occurrence)
"a" should be --as--.

Column 8, claim 1, line 21,

"ratio" should be --radio--.

UNITED STATES PATENT AND TRADEMARK OFFICE
CERTIFICATE OF CORRECTION

PATENT NO. : 5,408,315
DATED : April 18, 1995
INVENTOR(S) : Joel C. Mitchell, et al It is certified that error appears in the above-indentified patent and that said Letters Patent is hereby corrected as shown below:

Column 9, claim 13, line 64;

"or" should be --for--.

Column 10, claim 14, line 1;

"ratio" should be --radio--.

Signed and Sealed this

Nineteenth Day of December, 1995

*Attest:*

BRUCE LEHMAN

*Attesting Officer*      *Commissioner of Patents and Trademarks*